United States Patent [19]

Mark et al.

[11] 4,113,974

[45] Sep. 12, 1978

[54] PROCESS FOR PURIFYING IMPURE DIPHENOLS

[75] Inventors: Victor Mark, Evansville; Charles Vernon Hedges, Mt. Vernon, both of Ind.

[73] Assignee: General Electric Company, Pittsfield, Mass.

[21] Appl. No.: 755,981

[22] Filed: Dec. 30, 1976

[51] Int. Cl.$^2$ .................. C07C 37/22; C07C 37/24
[52] U.S. Cl. .................. 568/750; 260/607 AR; 260/609 F; 260/613 R; 568/749; 568/751; 568/755
[58] Field of Search ....... 260/619 A, 613 R, 607 AR, 260/609 F, 620

[56] References Cited

U.S. PATENT DOCUMENTS

| | | | |
|---|---|---|---|
| 2,829,175 | 4/1958 | Bowman et al. | 260/619 A |
| 2,845,464 | 7/1958 | Luten | 260/619 A |
| 2,959,622 | 11/1960 | Grimme et al. | 260/619 A |
| 3,073,868 | 1/1963 | Prahl et al. | 260/619 A |
| 3,207,795 | 10/1965 | Prahl et al. | 260/619 A |
| 3,290,391 | 12/1966 | Prahl et al. | 260/619 A |
| 3,326,986 | 6/1967 | Dugan et al. | 260/619 A |
| 3,535,389 | 10/1970 | De Jong | 260/619 A |
| 3,673,262 | 6/1972 | Prahl et al. | 260/619 A |
| 3,919,330 | 11/1975 | Kwantes et al. | 260/619 A |
| 3,932,535 | 1/1976 | Zoche et al. | 260/619 A |

*Primary Examiner*—Norman Morgenstern
*Attorney, Agent, or Firm*—Salvatore C. Mitri; William F. Mufatti

[57] ABSTRACT

A process for improving the quality of diphenols by recrystallization from aqueous solvent systems.

12 Claims, No Drawings

PROCESS FOR PURIFYING IMPURE DIPHENOLS

This invention relates to a process for purifying impure diphenols which comprises recrystallizing the impure diphenol from water in the presence of polar, aprotic co-solvents.

BACKGROUND OF THE INVENTION

It is well known that the purity of diphenols is of paramount importance regarding the quality of polymers which are prepared therefrom. Isomeric diphenols that often accompany the p,p'-diphenols are often deleterious since they do not participate as well in polymerization processes. It is thus desirable and important to obtain the p,p'-diphenols in their highest purity in order to secure the quality of the polymers which are prepared therefrom. Since isomeric diphenols always accompany the desired p,p'-diphenols, purification of the impure reaction products is always necessary.

In the past, purification of impure mixtures of p,p'-diphenols was most often affected by the use of organic solvents such as benzene, methylene chloride or toluene. The use of these and similar solvents results in costly purification due to both the cost of solvents and inefficiency of the method. Another purification method is set forth in U.S. Pat. No. 3,919,330. This method involves dissolving crude 2,2-bis(4-hydroxyphenyl)propane in ethylene glycol and then adding a certain amount of water whereby the 2,2-bis(4-hydroxyphenyl)propane is precipitated and is then recovered. However, this method requires the use of large amounts of ethylene glycol and the necessity of an additional step of separating the water from the aqueous mother liquor in order to recover and reuse the anhydrous glycol.

DESCRIPTION OF THE INVENTION

It has been discovered that p,p'-diphenols of high purity can be obtained by recrystallizing the impure p,p'-diphenol from water, in the presence of polar, aprotic co-solvents. One method to achieve this recrystallization comprises dispersing the impure p,p'-diphenol in water, heating the resulting slurry and then adding a water soluble polar, aprotic co-solvent until the dissolution or near dissolution of the diphenol results, at or near the boiling point of water or the solvent system. Subsequent cooling and recovery of the solids yields p,p'-diphenols of improved quality (assay).

Alternatively, the impure diphenols are heated with a premixed water and polar, aprotic co-solvent mixture, with stirring, until dissolution or near dissolution results, followed by cooling and subsequent recovery of the solid purified p,p'-diphenol.

The water soluble polar, aprotic co-solvents are those which neither yield a proton to the solute, nor gain one from it. Water soluble polar, aprotic co-solvents effective herein include amides, sulfoxides, sulfones, phosphoramides, sulfamides, nitriles, ethers and the like. Examples of these water soluble polar, aprotic co-solvents include dimethylformamide, dimethylacetamide, dimethylsulfoxide, dimethylsulfone, tetrahydrothiophene-1,1-dioxide, hexamethylphosphoramide, sulfamide, tetramethylsulfamide, tetramethylurea, dioxane, tetrahydrofuran, N-methylpyrrolidene, acetonitrile, etc. and mixtures thereof. Also, these water soluble polar, aprotic co-solvents may be used with the water soluble alcoholic or phenolic co-solvent, as described in co-pending application A, of Victor Mark and Charles Vernon Hedges Ser. No. 755,982, filed on the same date as the instant application and assigned to the same assignee as the present application, and/or with the watersoluble organic carboxylic acid, as described in co-pending application B, of Victor Mark and Charles Vernon Hedges Ser. No. 755,983 filed on the same date as the instant application and assigned to the same assignee as the present application. Applications A and B are incorporated herein by reference. Also, one or more of these polar, aprotic co-solvents and water may be employed simultaneously to accomplish recrystallization.

The amount of water soluble polar, aprotic co-solvent employed herein is dependent upon the amount of water used in the recrystallization, in that the higher the amount of water per solute, the greater the amount of co-solvent that will be required.

A wide variety of diphenols may be purified according to the method of the instant invention. These diphenols include 4,4'-thiodiphenol, 4,4'-oxydiphenol, cyclohexylidenediphenol, p,p'-biphenol, 2,2-bis(3,5-dimethyl-4-hydroxyphenyl)propane, as well as the corresponding tetrachloro and tetrabromo analogs, p,p'-sulfonyldiphenol, bis(3,5-dimethyl-4-hydroxyphenyl sulfone), and 2,2-bis(4-hydroxyphenyl)propane. In particular, the impure 2,2-bis(4-hydroxyphenyl)propane consists of a mixture of the p,p' and o,p' isomers and, depending on the method of preparation, of a host of other impurities. Some of these isomers are more soluble than the p,p' isomer and some are less so. It is, therefore, convenient to add to the aqueous slurry of the impure reaction mixtures just enough co-solvent that is necessary for the dissolution of the o,p' and p,p' isomer content of the mixture, leaving the lesser soluble components undissolved. The latter are conveniently removed by filtration. Subsequent cooling of the filtered solution deposits the less soluble p,p' isomer, leaving much or all of the more soluble p,p' isomer and other more soluble components in solution. Further cooling, preferably below ambient temperature of separation of the solvent mixture by distillation, often under reduced pressure, separates out or leaves behind the more soluble impurities.

The maximum temperature of the instant purification method is not critical, although sometimes it is determined by the boiling point of the lowest boiling co-solvent. When working at atmospheric pressure, it is desirable to stay near about 90° to 100° C so that the solvent properties of water can be best utilized. Since the solubility of diphenols increases dramatically with temperature, it is often advantageous to use superatmospheric pressure, such as those obtained by pressurizing the recrystallization vessels by inert gases or by employing autogeneous pressures. In some cases, 150° C or even higher temperatures are preferable, such as those available by the use of superheated steam.

It was found that the use of aqueous solvents results usually in the formation of well developed larger crystals, which can be readily separated by filtration. In the case of 2,2-bis(4-hydroxyphenyl)propane, the crystals have the rhombic crystal structure which may have on their surfaces a contamination of the more soluble isomeric impurities, usually the o,p' isomer. A simple slurrying or rinsing of these crystals by a proper solvent, such as methylene chloride, readily removes the impurities and leaves behind the crystals of the pure p,p' isomers.

DESCRIPTION OF THE PREFERRED EMBODIMENT

The following examples are set forth to illustrate more clearly the principle and practice of this invention to those skilled in the art. Unless otherwise specified, where parts or percents are mentioned, they are parts or percents by weight.

EXAMPLE I

To a one liter three necked flask, equipped with a stirrer, reflux condenser, addition funnel and thermometer, there was charged 50 grams of 2,2-bis(4-hydroxyphenyl)propane (bisphenol-A) and 500 ml. of water and the resultant slurry was heated with the aid of a heating mantel. When the water started to reflux, pure dimethylformamide was gradually added to the aqueous heterogeneous liquid until a clear solution resulted. It required 135.2 grams of the co-solvent formamide to yield a clear solution. Upon cooling to ambient temperature, with continuous stirring, well developed rhomboid crystals of p,p'-biphenol-A separated out, that were isolated by filtration in nearly quantitative yield.

EXAMPLES II to VI

The procedure of Example I was repeated exactly, except that dimethylformamide was replaced with the co-solvents and in the amounts shown in Table I.

TABLE I

Co-solvents Required to Dissolve 50 Grams of Bisphenol-A in 500 gms. of Water at 100° C

| Example | Co-solvent | Amount of Co-solvent (gms.) |
|---|---|---|
| II | Acetonitrile | 152.3 |
| III | Tetramethylurea | 259.4 |
| IV | Dioxane | 229.0 |
| V | Dimethylsulfoxide | 155.1 |
| VI | Tetrahydrothiophene-1,1-dioxide | 183.2 |

Obviously, other modifications and variations of the present invention are possible in the light of the above teachings. It is therefore to be understood that changes may be made in the particular embodiments of the invention described which are within the full intended scope of the invention as defined by the appended claims.

What is claimed is:

1. A process for purifying impure p,p'-diphenols which comprises dispersing the impure diphenol in water, heating the resulting slurry, adding a water soluble polar, aprotic co-solvent until the dissolution or near dissolution of the diphenol slurry results at or near the boiling point of water or the solvent system, cooling the solution to achieve the separation of the purified diphenol and recovering the purified p,p'-diphenol.

2. A process according to claim 1 wherein the polar, aprotic co-solvent is selected from the group consisting of amides, sulfoxides, sulfones, phosphoramides, sulfamides, nitriles and ethers.

3. A process according to claim 2 wherein the co-solvent is selected from the group consisting of dimethylformamide, dimethylsulfoxide, N-methylpyrrolidene and acetonitrile.

4. A process according to claim 1 wherein the impure diphenol is 2,2'-bis(4-hydroxyphenyl)propane.

5. A process according to claim 1 wherein the dissolution or near dissolution of the diphenol slurry results at about 90° to 100° C at atmospheric pressure.

6. A process according to claim 1 wherein the dissolution or near dissolution of the diphenol slurry is carried out at super-amtospheric pressure.

7. A process for purifying impure p,p'-diphenols which comprises dispersing the impure diphenol in a mixture of water and a water soluble polar, aprotic co-solvent or mixtures of co-solvents, heating the resultant slurry until the dissolution or near dissolution is achieved, cooling the solution to achieve the separation of the purified diphenol and recovering the purified p,p'-diphenol.

8. A process according to claim 7 wherein the polar, aprotic co-solvent is selected from the group consisting of amides, sulfoxides, sulfones, phosphoramides, sulfamides, nitriles and ethers.

9. A process according to claim 8 wherein the co-solvent is selected from the group consisting of dimethylformamide, dimethylsulfoxide, N-methylpyrrolidene and acetonitrile.

10. A process according to claim 7 wherein the impure diphenol is crude 2,2'-bis(4-hydroxyphenyl)propane.

11. A process according to claim 7 wherein the dissolution or near dissolution of the diphenol slurry results at about 90° to 100° C at atmospheric pressure.

12. A process according to claim 7 wherein the dissolution or near dissolution of the diphenol slurry is carried out at super-atmospheric pressure.

* * * * *